United States Patent [19]

Margerum et al.

[11] Patent Number: 5,976,493
[45] Date of Patent: Nov. 2, 1999

[54] METABOLICALLY CLEAVABLE DENDRIMERIC POLYCHELANTS

[75] Inventors: Lawrence Margerum, San Ramon; Joan Carvalho, Mountain View; Martha Garrity, Oakland; Jere Douglas Fellmann, Livermore, all of Calif.

[73] Assignee: Nycomed Salutar, Inc., Wayne, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/702,693

[22] PCT Filed: Mar. 3, 1995

[86] PCT No.: PCT/GB95/00464

§ 371 Date: Nov. 8, 1996

§ 102(e) Date: Nov. 8, 1996

[87] PCT Pub. No.: WO95/24225

PCT Pub. Date: Sep. 14, 1995

[30] Foreign Application Priority Data

Mar. 4, 1994 [GB] United Kingdom ............... 9404208

[51] Int. Cl.⁶ .................. A61K 51/04; A61K 49/00; A61B 5/055
[52] U.S. Cl. .............. 424/1.65; 424/1.69; 424/9.3; 424/9.361; 424/9.36; 424/DIG. 16
[58] Field of Search ................ 424/1.65, 1.49, 424/1.69, 1.53, 9.3, 9.322, 9.361, 9.363, DIG. 16, 484, 9.36; 534/10, 14, 15, 16; 540/474, 465; 546/2

[56] References Cited

U.S. PATENT DOCUMENTS 5,338,532  8/1994  Tomalia et al. ............... 424/1.49
5,364,614  11/1994  Platzek et al. ............... 424/9.3

FOREIGN PATENT DOCUMENTS

WO 90/12
050  10/1990  WIPO .
WO 91/05
762  5/1991  WIPO .
WO 93/06
868  4/1993  WIPO .
WO 95/07
270  3/1995  WIPO .

Primary Examiner—Jose' G. Dees
Assistant Examiner—Michael G. Hartley
Attorney, Agent, or Firm—Fish & Richardson P.C.

[57] ABSTRACT

The invention provides polychelant compounds which are useful for example in diagnostic imaging procedures and which are degradable in vivo to release excretable fragments. Such compounds conveniently are of the formula (I): $R^1(X^1R^2((X^2)_pL)_n)_m$ (where $X^1$ is a linker moiety metabolically cleavable to release $R^1X^3_m$ and $X^4R^2((X^2)_pL)_n$ fragments where $X^3$ and $X^4$ are the cleavage residues of $X^1$; $R^1X^3_m$ is a biotolerable polymer, preferably a substantially monodisperse polymer and especially one with a molecular weight below 40,000 D, particularly below 30,000 D and especially below 20,000 D, for example a first to sixth generation dendrimer; $X^4R^2((X^2)_pL)_n$ is a polychelant fragment having a molecular weight below 40,000 D, preferably below 30,000 D, especially below 20,000 D, each such moiety preferably being the same; p is 0 or 1; $X^2$, where present, is a linker moiety metabolically cleavable to release a monochelant fragment; each L is a macrocyclic chelant moiety, wherein the macrocyclic skeleton preferably has 9 to 25 ring members and preferably is an optionally oxygen or sulphur interrupted polyazacycloalkane; $R^2((X^2)_p)_n$ is a straight chain or branched backbone moiety, preferably providing a chain of up to 20 atoms between each L group and the $X^1$ moiety to which it is joined and a chain of up to 25 atoms between each pair of L groups linked thereby, such chains conveniently being nitrogen and/or oxygen and/or sulphur interrupted carbon chains; each n is an integer having a value of at least 2, preferably a value of 2 to 25, especially 2 to 12; and each m is an integer having a value of at least 2, preferably a value of up to 200, especially 3 to 100, such that the total number of L groups in the polychelant of formula (I) is at least 20, preferably 50 to 200), having a molecular weight of at least 30,000 D, preferably at least 40,000 D, and especially preferably 50,000 to 150,000 D, and metal chelates and salts thereof.

14 Claims, No Drawings

METABOLICALLY CLEAVABLE DENDRIMERIC POLYCHELANTS

RELATED APPLICATIONS

This application is a 371 of PCT/GB95/00464, filed Mar. 3, 1995.

This invention relates to polychelants, as well as the corresponding bifunctional polychelants (eg site-directed macromolecular conjugates of the polychelants, and the chelates and salts thereof and their applications in medicine, especially in the field of diagnostic imaging.

The polychelates are especially suited for use in enhancing images of selected mammalian organs, tissues, cells, and the like, in vivo, using Magnetic Resonance Imaging (MRI), X-ray, gamma scintigraphy, and CT scanning, by virtue of their enhanced imaging properties and site specificity. The polychelants are also particularly well suited for use as intravascular contrast agents, blood pool agents, in these imaging modalities. As such they may be used in imaging blood vessels, e.g. in magnetic resonance angiography, in the measurement of blood flow and volume, in the identification and characterization of lesions by virtue of differences in vascularity from normal tissue, in the imaging of the lungs for the evaluation of pulmonary disease and in blood perfusion studies. The polychelants are also well suited for metal detoxification, therapeutic delivery of radioisotopes and diagnostic nuclear medicine applications.

Medical imaging modalities, such as MRI, X-ray, gamma scintigraphy, and CT scanning, have become extremely important tools in the diagnosis and treatment of illnesses. Some imaging of internal parts relies on inherent attributes of those parts, such as bones, to be differentiated from surrounding tissue in a particular type of imaging, such as X-ray. Other organs and anatomical components are only visible when they are specifically highlighted by particular imaging techniques.

One such technique with potential to provide images of a wide variety of anatomical components involves biotargeting image-enhancing metals. Such a procedure has the possibility of creating or enhancing images of specific organs and/or tumors or other such localized sites within the body, while reducing the background and potential interference created by simultaneous highlighting of non-desired sites.

Researchers have recognized for many years that chelating various metals increases the physiologically tolerable dosage of such metals and so permits their use in vivo to enhance images of body parts (see for example C. D. Russell and A. G. Speiser, J. Nucl. Med. 21: 1086 (1988) and U.S. Pat. No. 4,647,447 (Gries et al.)). However, such simple metal chelate image enhancers, without further modification, do not generally provide any particularly significant site specificity.

The attachment of metal chelates to tissue or organ targeting molecules, e.g. biomolecules such as proteins, in order to produce site specific therapeutic or diagnostic agents has been widely suggested.

Many such bifunctional chelating agents, i.e. agents which by virtue of the chelant moiety are capable of strongly binding a therapeutically or diagnostically useful metal ion and by virtue of the site-specific molecular component are capable of selective delivery of the chelated metal ion to the body site of interest, are known or have been proposed in the literature. Thus for example even relatively early publications in the field of MRI contrast agents, such as GB-A-2169598 (Schering) and EP-A-136812 (Technicare) suggested the use as contrast agents of paramagnetic metal ion chelates of bifunctional chelants.

The attachment of chelant moieties to site-specific macromolecules has been achieved in a number of ways, for example the mixed anhydride procedure of Krejcarek et al. (Biochemical and Biophysical Research Communications 77: 581 (1977)), the cyclic anhydride procedure of Hnatowich et al. (see Science 220: 613 (1983) and elsewhere), the backbone derivatisation procedure of Meares et al. (see Anal. Biochem. 142: 68 (1984) and elsewhere—this is a technique used by Schering in EP-A-331616 to produce site specific polychelates for use as MRI or X-ray contrast agents), and the linker molecule procedure used for example by Amersham (see WO-A-85/05554) and Nycomed (see EP-A-186947 and elsewhere) to produce paramagnetic metal ion chelates of bifunctional chelants for use as MRI contrast agents.

Thus, Krejcarek et al (supra) disclosed how polyaminopolycarboxylic acid (PAPCA) chelants, specifically DTPA (diethylenetriaminepentaacetic acid) could be conjugated to a protein, such as human serum albumin (HSA), by reaction of the triethylamine salt of the PAPCA with isobutylchloroformate. (IBCF) and by reacting the IBCF-PAPCA adduct with the protein. Their aim was to attach one radioactive metal per human serum albumin molecule for the purpose of measuring biological function.

Site specific uses of various imaging techniques all require or would be enhanced by use of a multiplicity of the appropriate metal ion conjugated to a site-directed macromolecule. For example, it is believed that a 50% reduction in $T_1$ relaxation time of water protons in a target tissue is a requirement for an effective MRI contrast agent. Considering the affinity of antibodies for their antigens and the concentration of these antigens in the target tissues, it has been calculated that each antibody molecule must carry a number of paramagnetic centers to bring about these levels of $T_1$ reduction. (see Eckelman, et al., NATO ASI Series, Series A, 152:571 (1988)).

Unger et al. in Investigative Radiology 20:693 (1985) analyzed tumor enhancement for magnetic resonance imaging using an anti-CEA monoclonal antibody conjugated with Gd-DTPA. They found no tumor enhancement when 4 Gd atoms were bound per antibody molecule, and predicted that a far greater ratio of imaging metal atoms per macromolecule would be required to be effective.

Likewise, Schreve and Aisen in Mag. Res. in Medicine 3:336 (1986), concluded that the concentrations of paramagnetic ion which could be delivered to a tumor using the described technology would result in large doses for humans, making this approach to imaging highly limited in its use.

For site specific image enhancement however it is important that the site specificity of the tissue or organ targeting moiety of such chelates of bifunctional chelants should not be destroyed by conjugation of the chelant moiety. Where the bifunctional chelant contains only one chelant moiety this is not generally a severe problem; however when attempts have been made to produce bifunctional polychelants by conjugating several chelant moieties onto a single site-specific macromolecule, it has been found not only may the maximum achievable chelant: site-specific macromolecule ratio be relatively limited but as the ratio achieved increases the site-specificity of the resulting bifunctional polychelant decreases.

Numerous attempts have nonetheless been made to produce bifunctional polychelants with increased numbers of chelant moieties per site-specific macromolecule.

Thus Hnatowich et al. (supra) used the cyclic anhydride of the chelant DTPA to attach it to a protein.

This is a relatively simple one-step synthesis procedure which as a result has been used by many other researchers. However, due to the presence of two cyclic anhydride groups in the starting material, widespread cross-linking of the macromolecules can lead to the production of conjugates that can not readily be characterized (see Hnatowich et al., J. Immunol. Methods 65:147 (1983)). In addition, this procedure suffers from the same drawback as that for Krejcarek's mixed anhydride method in that the uncontrolled addition of more than a few chelant moieties destroys the site-specificity of the macromolecule to which they are linked. (See also Paik et al. J. Nucl. Med. 25:1158 (1983)).

In order to overcome the problems of attaching larger numbers of chelant moieties to a site-specific macromolecule without destroying its site-specificity, i.e. without disturbing its binding site(s), there have been many proposals for the use of a backbone molecule to which large numbers of chelant moieties can be attached to produce a polychelant one or more of which can then be conjugated to the site-specific macromolecule to produce the bifunctional polychelant.

The by now conventional cyclic anhydride conjugation technique of Hnatowich et al. (supra) has thus been used to produce bifunctional polychelants in which the chelant moieties are residues of open chain PAPCAs, such as EDTA and DTPA, and in which the backbone molecule is a polyamine such as polylysine or polyethyleneimine. Thus for example Manabe et al. in Biochemica et Biophysica Acta 883: 460–467 (1986) reported attaching up to 105 DTPA residues onto a poly-L-lysine backbone using the cyclic anhydride method and also attaching polylysine-polyDTPA polychelants onto monoclonal antibody (anti-HLA IgG$_1$) using a 2-pyridyl disulphide linker achieving a substitution of up to about 42.5 chelants (DTPA residues) per site-specific macromolecule. Torchlin et al. in Hybridoma 6:229–240 (1987) also reported attaching DTPA and EDTA to polyethyleneimine and polylysine backbones which were then attached to a myosin-specific monoclonal antibody, or its Fab fragment, to produce bifunctional polychelants for use in MRI or scintigraphy.

While Manabe and Torchlin have reported the production of bifunctional polychelants, the cyclic anhydride route adopted by Manabe poses cross-linking and hence characterization problems and Torchlin et al in their conclusion doubted that their technique would enable the paramagnetic metal concentration to be increased sufficiently to permit MRI of tumours.

Sieving et al. in WO-A-90/12050 disclosed techniques for producing polychelants comprising macrocyclic chelating moieties, such as polylysine-polyDOTA, and for the preparation of corresponding bifunctional polychelants. Sieving et al. also suggested the use of starburst dendrimers, such as the sixth generation PAMAM starburst dendrimer of Tomalia et al. (see U.S. Pat. No. 4587329 and Polymer Journal 17:117 (1985)), as the skeleton for such polychelants.

The drive towards higher metal loading capacity in the production of polychelants has resulted in high molecular weight products being produced. For soluble products, this does have the advantage that on administration into the circulatory system the compounds are retained within the blood rather than diffusing rapidly into the extracellular fluid or being excreted by glomerular filtration. Accordingly, these compounds can serve as effective blood pool imaging agents. However, it is nevertheless undesirable that the polychelates should remain in the body for longer than necessary, for example after imaging is complete. The present invention resides in part in the realisation that polychelates can be produced which are diagnostically or therapeutically effective and yet are readily metabolised to fragments which may be rapidly excreted, for example by glomerular filtration, following metabolic cleavage of well characterised polychelate fragments therefrom. The incorporation within the overall polychelant structure of cleavable polychelant fragments has added advantages in that the number of chelant groups that can be added to each attachment site on the backbone polymer is increased and that polychelates can be produced by conjugating already metallated polychelant sub-units onto a backbone polymer thereby improving the metal loading ratio for the completed polychelant.

Thus, viewed from one aspect, the invention provides a polychelant of formula I $$R^1(X^1R^2((X^2)_pL)_n)_m \qquad (I)$$

(where

X$^1$ is a linker moiety metabolically cleavable to release $R^1X^3{}_m$ and $X^4R^2((X^2)_pL)_n$ fragments where X$^3$ and X$^4$ are the cleavage residues of X$^1$;

$R^1X^3{}_m$ is a biotolerable polymer, preferably a substantially monodisperse polymer and especially one with a molecular weight below 40,000 D, particularly below 30,000 D and especially below 20,000 D, for example a first to sixth generation dendrimer;

$X^4R^2((X^2)_pL)_n$ is a polychelant fragment having a molecular weight below 40,000 D, preferably below 30,000 D, especially below 20,000 D, each such moiety preferably being the same;

p is 0 or 1;

X$^2$, where present, is a linker moiety metabolically cleavable to release a monochelant fragment;

each L is a macrocyclic chelant moiety, wherein the macrocyclic skeleton preferably has 9 to 25 ring members and preferably is an optionally oxygen or sulphur interrupted polyazacycloalkane;

$R^2((X^2)_p)_n$ is a straight chain or branched backbone moiety, preferably providing a chain of up to 20 atoms between each L group and the X$^1$ moiety to which it is joined and a chain of up to 25 atoms between each pair of L groups linked thereby, such chains conveniently being nitrogen and/or oxygen and/or sulphur interrupted carbon chains;

each n is an integer having a value of at least 2, preferably a value of 2 to 25, especially 2 to 12; and each m is an integer having a value of at least 2, preferably a value of up to 200, especially 3 to 100, such that the total number of L groups in the polychelant of formula (I) is at least 20, preferably 50 to 200), having a molecular weight of at least 30,000 D, preferably at least 40,000 D, and especially preferably 50,000 to 150,000 D, and metal chelates and salts thereof.

The term "polychelant" is used hereinafter, wherever the context permits, to designate not only the unmetallated compound but also its fully and partially metallated forms.

If desired, one or more polychelants according to the invention may be conjugated to a biodistribution modifier, ie. a moiety which serves to alter the pharmacokinetics of the overall molecule, eg. a hydrophilic moiety or a site-directed molecule, for example a protein or protein fragment, to form a bifunctional polychelant. In this event, the linkage with the site-directed molecule is preferably also metabolically cleavable so that biodegradation of the bifunctional polychelant will liberate the site-directed molecule (or its metabolites) as well as fragments of the polychelant. These bifunctional polychelants form a further aspect of the present invention and may be used, for example, to enhance images and/or to deliver cytotoxic doses of radioactivity to targeted cells, tissues, organs and/or body ducts. Alternatively, the polychelants may be used as blood pool agents without being coupled to site-directed molecules.

The polychelants are in and of themselves useful entities in medical diagnosis and therapy, due in part to their unique localisation within the body. The monomeric chelates presently used for MR imaging contrast enhancement (for example $GdDTPA^{2-}$, $GdDOTA^{1-}$ and GdDTPA-BMA) have in vivo applications limited to their specific rapid biodistribution which causes localisation of these chelates throughout the extracellular (and extravascular) spaces of the body. The polychelants of the invention, which typically have molecular weights of 30 to 200 kD, especially 40 to 150 kD, and particularly 50 to 120 kD, have radically altered biodistribution relative to the monochelants. The polychelants of the invention generally have extended intravascular residence times, generally of the order of hours; however by virtue of their biodegradability they can generally eventually clear into the extracellular fluid (ECF) and undergo renal excretion. Thus as these polychelants, hereafter referred to as magnifiers, remain primarily in the intravascular system for a diagnostically useful residence time, they are suitable for a range of uses such as blood pool and cardiac perfusion imaging, cerebral imaging, blood vessel imaging, in the imaging of the lungs for the evaluation of pulmonary disease, CNS tumour detection and volume determination and thrombus detection and angiography. As blood pool agents, they are particularly suited to use in studies of blood flow or volume, especially in relation to lesion detection and myocardial perfusion studies. Conventional monomeric MR imaging contrast agents which rapidly disperse into the extracellular/extravascular space, cannot readily be used for these purposes. Moreover, in view of their enhanced relativity, the MR imaging contrast agents of the invention can be administered at significantly reduced dosages relative to current monomeric MR imaging contrast agents such as GdDTPA, GdDOTA and GdDTPA-BMA, thus providing a significantly improved safety margin in their use.

It is particularly preferred that all of the metabolic degradation products of the polychelant of the invention, in particular the polymer $R^1X^3_m$ and the polychelant fragments $X^4R^2((X^2)_pL)_n$, be of sufficiently low molecular weight that they are renally excretable even though the non-degraded polychelant may itself have a molecular weight sufficiently high that it is not. Similarly, it is preferred that the polychelant (and its chelates) be water soluble so that it can function as a blood pool agent. For a blood pool agent, one requires a molecule having a size or overall molecular weight sufficiently large that blood capillary filtration is sufficiently slow that blood pool image contrast can be obtained. By analogy with globular proteins, the kidney threshold (the minimum molecular weight) can generally be considered to lie in the range 30 to 40 kD. Molecular size and configuration is of course more important than overall molecular weight but these minimum molecular weights (for the unmetallated polychelant) do provide a reasonably accurate guideline. Thus the invention provides one way in which one can construct a well characterised blood pool agent which will itself biodegrade into well characterised, readily and usually renally, excretable fragments. In this way, the build up within the body of the potentially toxic diagnostic or therapeutic metal ions with which the polychelant is loaded is reduced.

The polymeric backbone ($R^1$) onto which the polychelant fragments are mounted is itself preferably substantially monodisperse so that the biodistribution of the polychelant is uniform and so that a uniform and reproducible metal loading ratio can be achieved. By the metal loading ratio is meant the ratio between the number of therapeutic or diagnostic metal ions carried by the macrocyclic chelant groups and the number of polychelant molecules.

Virtually any biotolerable polymer which has attachment points (for example in-chain or pendant reactive functional groups such as amines, hydroxyls, carboxyls, etc) for the polychelant fragments ($R^2((X^2)_pL)_n$) may be used, for example polylysine, polyethyleneimine, polysaccharides, etc. However, it is particularly preferred to use dendrimeric polymers and especially the so-called starburst dendrimers, since these may be produced in substantially monodisperse and well characterised form and since the dendrimeric structure facilitates uniform loading of the polychelant fragments onto the attachment points on the polymer backbone as these tend to be disposed about the periphery of the dendrimeric molecule. With starburst dendrimers, this is particularly so and their substantially spherical shape provides the maximum water access to the chelated metal ions as well as allowing optimal metallation efficiency, i.e. maximum metal loading.

The dendrimers which are particularly suited to use according to the invention as the polymeric backbone $R^1$ include the first to sixth generation dendrimers. The optimum generation depends of course on the nature of the polychelant fragment, the intended administration and elimination route, etc. Suitable backbone polymers, including starburst dendrimers, are discussed at length in earlier patent applications such as WO-A-91/05762, WO-A-90/12050, and PCT/EP92/02308, as well as by Tomalia et al. in U.S. Pat. No. 4,587,329, U.S. Pat. No. 4,568,737, U.S. Pat. No. 4,558,120, U.S. Pat. No. 4,507,466, WO-A-88/01178 and Angew Chem Int Ed Eng 29:138–175 (1990).

Where a contrast agent is required to collect in the blood pool, then preferably a low generation dendrimeric backbone will be used, for example a fourth or fifth generation dendrimeric backbone. Such polychelants have enhanced relaxivity compared to known blood pooling and ECF contrast agents and thus a lower effective dosage can be administered.

The metabolically cleavable linker moieties $X^1$ and $X^2$ may be or incorporate any functional group which is cleaved in vivo following administration, generally parenteral administration. The degree of susceptibility to cleavage can be selected by appropriate selection of these linker moieties so as to achieve a desired half life before breakdown, for example a desired blood residence time, or so as to ensure that breakdown occurs predominantly at particular body sites such as the liver. Ester, disulphide, amide, acetal, ketal, ether, anhydride and lactam functionalities are examples of groups which may be considered to by hydrolysable or otherwise biodegradable. Depending upon the desired breakdown site, it may be desirable to incorporate within the polychelant fragments moieties which are biotargeting, eg. hydrophilic, lipophilic or charged, so as to assist in post-cleavage clearance.

It is particularly preferred that metabolically cleavable $X^1$ groups occur at the points of attachment during synthesis of pre-formed polychelant groups (i.e. of $R^2((X^2)_pL)_n$ moieties). Thus while it would be possible to conjugate monomeric macrocyclic chelant groups onto a preformed skeleton, it is preferable according to the invention to conjugate preformed polychelant moieties onto a backbone polymer. For a given backbone polymer, this synthetic route leads to polychelants which have multiple chelant moieties per attachment site to the backbone and as a result have a high loading ratio for the metallated product. This moreover has the advantage that bulky dimeric, trimeric or higher oligomeric polychelant fragments will have restricted rotation at the attachment site to the polymer backbone so leading to greater relaxivities where the overall polychelant is a $T_1$ MR imaging contrast agent.

In this regard it is particularly preferred to use preformed dimeric or dendrimeric polychelant fragments which incorporate an active site for attachment to a polymeric or dendrimeric backbone polymer. Where the conjugation site, on conjugation, does not itself produce a metabolically cleavable bond, then a metabolically cleavable functional linker moiety should be incorporated within the preformed polychelant fragment or within the backbone polymer. In this regard, urea, ether, ester, double ester, carbamate, disulphide or other hydrolytically cleavable groups may be incorporated, for example in the preformed polychelant fragment between the polychelant backbone and the reactive group by which it is to be joined to the polymeric backbone of the overall polychelant. Alternatively, these cleavable groups may be located between the monochelant moieties so that on metabolic fragmentation monochelants or other small polychelant fragments may be released. Polychelants of this nature form a further aspect of the invention and are of formula II

$$R^1(X^1R^2((X^2)_pL)_n)_m \qquad (II)$$

(where $R^1$, $R^2$, L, p, n and m are as defined above, and $X^1$ and $X^2$ are linker moieties with the proviso that between each L and $R^1$ at least one of the linking $X^2$ and $X^1$ moieties is metabolically cleavable) and metal chelates and salts thereof as well as corresponding bifunctional polychelants.

Thus in preferred aspects of the invention, the backbone $R^2((X^2)_p)_n$ of the polychelant fragment comprises a branched polyalkane chain itself optionally incorporating homo or heterocyclic saturated or unsaturated rings (for example 5 to 8 membered rings incorporating 0, 1 or 2 heteroatoms selected from O, N and S, e.g. phenyl rings), nitrogen, oxygen or sulphur atoms or carbonyl groups, the latter preferably being adjacent chain heteroatoms.

Examples of preformed polychelant fragments include the following:

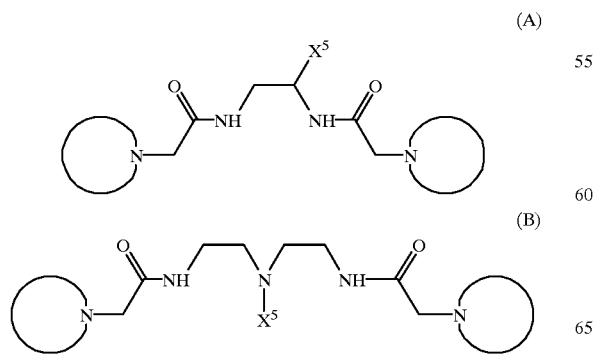

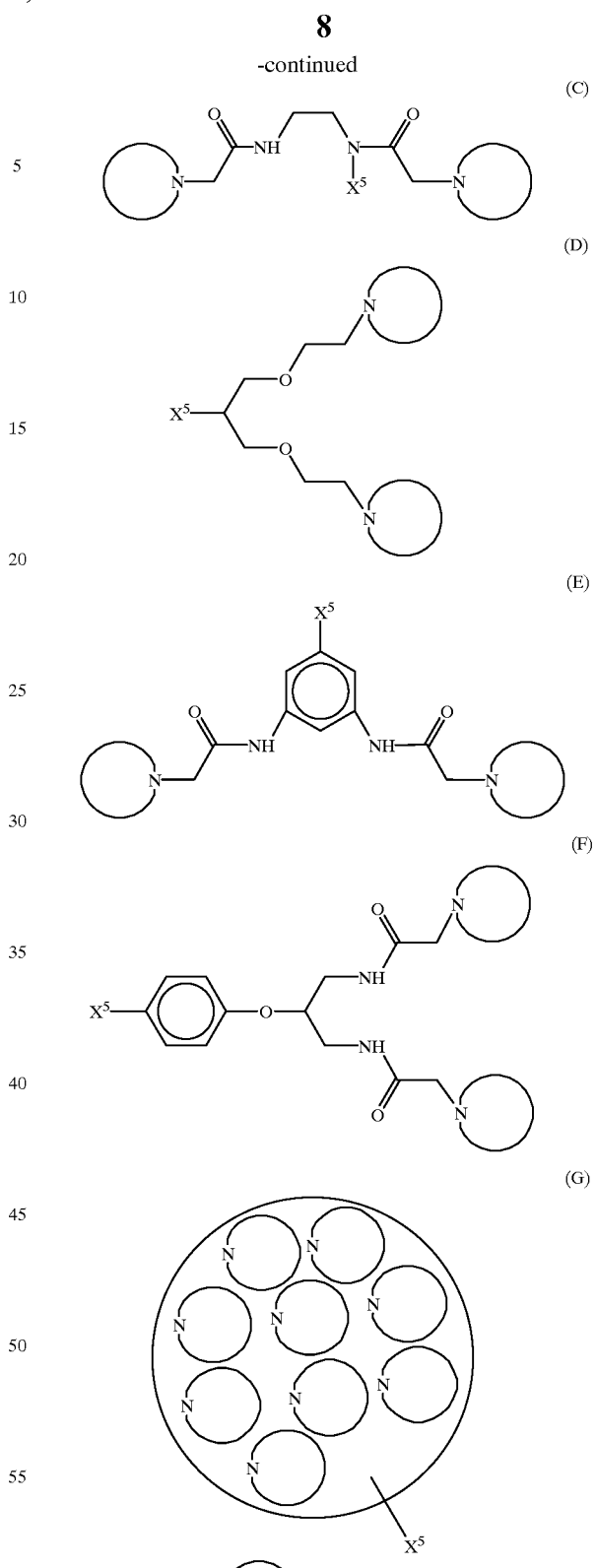

where $X^5$ is a group providing an appropriate site for attachment to the central skeletal structure, eg. a modified amine group linkable to an amine function, for example $X^5$ may be a group

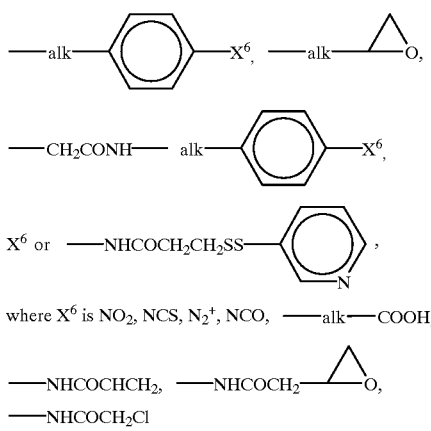

where $X^6$ is $NO_2$, NCS, $N_2^+$, NCO, —alk—COOH,

—NHCOCHCH$_2$, —NHCOCH$_2$—△—O,

—NHCOCH$_2$Cl or —NHCOCH$_2$Br and alk is a bond or a $C_{1-4}$ alkylene chain and

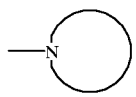

is a metallated or non-metallated macrocyclic chelant moiety preferably but not essentially attached to the rest of the structure at a ring nitrogen of the macrocycle.

The macrocyclic chelant moieties in the polychelants of the invention may be residues of any of the conventional macrocyclic chelants such as for example DOTA, TETA, DO3A, etc. The macrocyclic skeleton, as mentioned above, preferably has 9 to 25 ring members and conveniently is an optionally oxygen or sulphur interrupted polyazacycloalkane ring. The attachment site for the polychelant fragment $R^2((X^2)_p)_n$ is preferably a ring nitrogen but alternatively attachment may be at a ring carbon, for example as described by Meares et al in U.S. Pat. No. 4,687,667.

The macrocyclic chelant moiety may rely solely on its ring heteroatoms for its chelating ability and thus may be a cyclic polyether or polyamine. However the macrocyclic chelant moieties preferably have pendent groups which participate in metal chelation, for example $C_{1-6}$ alkyl groups carrying hydroxyl, amino, phosphonate, or phosphinate or more preferably carboxyl groups. DO3A and DOTA derived macrocycles are especially preferred, i.e. groups of formula . . .

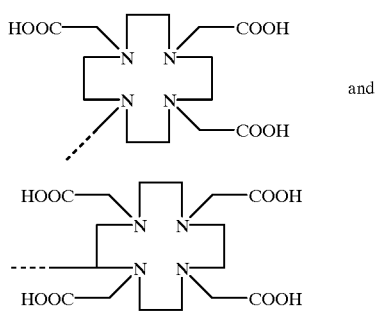

The macrocyclic chelant moieties in the polychelants of this invention preferably derive from macrocyclic chelants which have a reactive carboxyl or amine group which is not essential for metal coordination bonding. The reactive group can be one of the groups which in the free chelant can function as a metal coordinating group so long as the conjugated chelant moiety retains the ability to complex metal ions. Alternatively the reactive group can be a substituent on a side chain of the chelant or on a backbone carbon.

More particularly, as used herein, a macrocyclic chelant is defined as a chelant having one continuous, linked, closed backbone consisting of donor atoms, such as for example N, P, B, O, S and As, spaced by carbon atoms e.g. carbons of optionally substituted methylene or cyclic, e.g. aromatic, groups or chains thereof, particularly preferably optionally substituted $C_{2-4}$ alkylene chains. Any of the methylene groups or donor atoms, where permitted by valence conditions, can be substituted so long as the closed chain of the macrocycle remains intact.

In one preferred embodiment of the invention, the macrocyclic chelants are of formula III

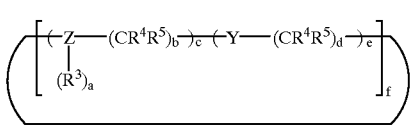

(III)

where a, b, d and e are independently zero or a positive integer, for b or d preferably 1, 2, 3 or 4; c and f are positive integers; the sum of all c's being at least 3, preferably 3, 4 or 5; the sum of b+d is at least 1;

each Z is independently a nitrogen, oxygen, sulphur, phosphorus, boron or arsenic, preferably at least two, especially at least 3 of these being nitrogen; each Y is independently an optionally substituted 5 to 7 membered carbocyclic or heterocyclic ring;

$R^3$ where present is independently hydrogen, optionally hydroxylated, optionally alkoxylated alkyl optionally carrying a group CO—G where G is $OR^4$ or $NR^4_2$ and where Z is phosphorus optionally also oxo, at least 3 $Z(R^3)_a$ moieties preferably having Z as nitrogen, a=1 and $R^3$ as an optionally substituted G—CO-alkyl group;

$R^4$ and $R^5$ which may be the same or different each independently is hydrogen, optionally alkoxylated, optionally hydroxylated alkyl, aryl, alkaryl or aralkyl or $R^5$ may also represent or be substituted by a group CO—G; and $NR^4_2$ may also represent a nitrogen-attached optionally substituted 5 to 7 membered heterocyclic ring optionally containing a further nitrogen oxygen, or sulphur ring heteroatom; and where in place of two $CR^4R^5$ groups, separated in either direction by at least one Z group, there may optionally be a bridging structure of formula

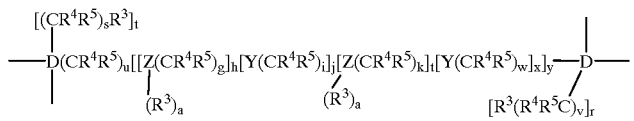

where u, g, h, i, j, k, l, w, x, q, r, s and t is each independently zero or a positive integer, for u, g, i, k and w preferably 1, 2, 3 or 4; y is a positive integer; $h+l+j+x \geq 1$, preferably $y(h+l) \geq 1$; and each D is independently boron, carbon, nitrogen, phosphorus or PO.

Preferred identities for the ring moieties Y include

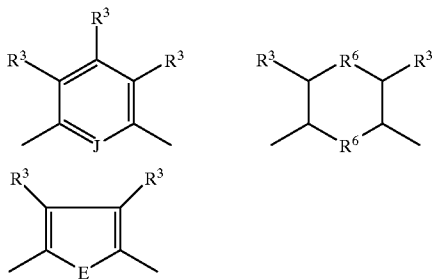

where
J is CH, COH or N;
$R^6$ is $CH_2$, CHOH, $NR^3$, O or S; and
L is O or S.

Preferred identities for the heterocyclic moieties $NR^4_2$ include

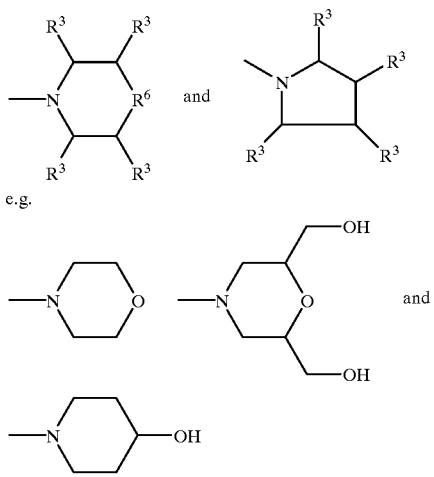

As indicated above, the macrocyclic chelant may include a second "cycle" which is created by linking the branches from two or more backbone atoms.

In the macrocyclic chelants, alkyl and alkylene moieties, unless specified otherwise, preferably contain up to 8 carbon atoms, especially preferably up to 4 carbons. Hydroxy or alkoxy substituted moieties may be mono- or poly-substituted and substitution by both is contemplated. Any aryl moieties are preferably $C_{6-10}$ carbocyclic or 5 or 6 membered heterocyclic rings. In the macrocycle, backbone heteroatoms, e.g. N, P, O and S are preferably separated by 1 to 8, especially preferably 2 to 6 carbon backbone atoms and, as mentioned, the macrocyclic chelant preferably contains at least 3 carboxyl groups or carboxyl derivative groups. Macrocyclic polychelants containing at least three ring nitrogen attached carboxyalkyl, especially carboxymethyl, groups are particularly preferred.

Linkage of the macrocyclic chelant to the backbone moiety $R^2((X^2)_p)_n$ may be effected through any reactive group, e.g. an $R^3$ or $R^5$ group, particularly preferably a CO—G group-containing $R^3$ group. Reaction of macrocycles with protonated ring heteroatoms (e.g. in DO3A) with

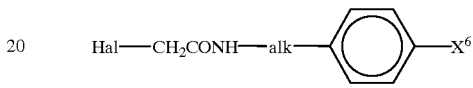

(where Hal is a halogen atom and alk and $X^6$ are as defined above), or with $Hal—CH_2CO_2CH_3$ and then with a diamine such as ethylene-diamine, provides a reactive group for linkage to the dendrimeric backbone. Other standard coupling techniques can be used and thus the macrocyclic chelating moieties in the polychelants of the invention preferably comprise the residues of a chelant of formula III (i.e. groups of formula III but with one of the ring attached substituents modified or replaced to provide a link to the dendrimer).

Conveniently the macrocyclic chelant is the residue of a polyazacycloalkane having 3, 4, 5 or 6 (preferably 4) ring nitrogens each separated by 2, 3 or 4 (preferably 2) ring carbons. Particularly preferred backbone structures for the macrocyclic chelant moieties include the following:

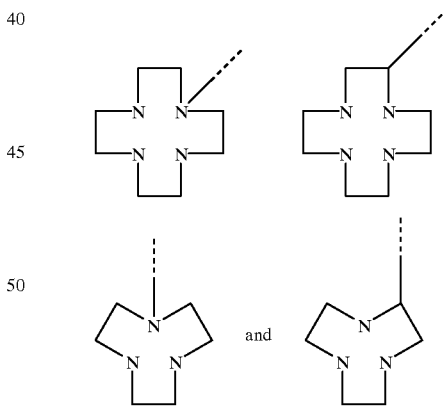

Particularly preferred macrocyclic chelants include those of formula IV (IV)

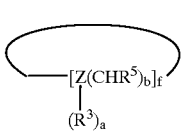

where each Z is N, O or S, preferably all or all but one Z being N;

each b is independently 2, 3 or 4, preferably 2 or 3;

f is 3 or 4, preferably 4;

each $R^3$ is independently hydrogen, $C_{1-3}$ alkyl or an optionally branched, optionally hydroxylated CO—G-alkyl group; and each $R^5$ is independently hydrogen or a hydroxyalkyl group.

Thus in particular, the macrocyclic chelants include the polyazacycloalkanepolycarboxylates, hexaazamacrocycles (HAMs) and cryptates including sepulchrates and sarcophagines.

Exemplary polyazacycloalkanepolycarboxylates include 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecanetriacetic acid (DOXA), 1,4,7-triazacyclononanetriacetic acid (NOTA) and 1,4,8,11-tetraazacyclotetradecanetetraacetic acid (TETA). Additionally, the novel tetraazacycloalkanepolycarboxylates, DOTA-N(2-aminoethyl)amide and DOTA-N(4-aminophenethyl)amide are also contemplated.

The preparation of the tetraazacycloalkanepolycarboxylate ligands is well known. Synthesis of DOTA is described in U.S. Pat. No. 4,647,447 (Gries et al.), U.S. Pat. No. 4,639,365 (Sherry) and by Desreux et al. in Inorg. Chem. 19:1319 (1980). Additionally, DOTA is available commercially from Parish Chemical Co., Orem, Utah, U.S.A. Preparation of DO3A is described in EP-A-292689 (Squibb). Desreux, Inorg. Chem., 19:1319 (1980); Bryden et al, Anal. Chem, 53:1418 (1981); Delgardo et al, Talanta, 29:816 (1982); Cacheris et al, Inorg. Chem, 26:958 (1987); Moi et al, Inorg. Chem, 26:3458 (1987) and Meares et al, Acc. Chem. Res., 17:202 (1984) describe the properties and chemistry of the macrocyclic ligands DOTA, NOTA, TETA and their backbone-derivatized analogues, including the preparation of NOTA and TETA. U.S. Pat. No. 4,678,667 (Meares et al.) teaches the preparation of a number of macrocyclic, side chain-derivatized ligands including DOTA and TETA. Derivatization of DOTA to form DOTA-N(2-aminoethyl)amide and DOTA-N(4-aminophenethyl)amide is described in detail hereinafter in Examples 2 and 3, respectively. The above cited references and all other references mentioned herein are hereby incorporated by reference in their entirety.

The hexaazamacrocycles include the series of N6 macrocyclic chelates described in DeCola et al. in Inorg. Chem. 25:1729 (1986). That article also describes preparation of the HAMs and is incorporated herein by reference in its entirety.

Cryptates are polycyclic ligands which include sepulchrates, sarcophagines and macrocyclic polyethers (crown ethers) and macrobicyclic ligands. Preferred macrocyclic polyether cryptates include side-chain derivatized primary amine and carboxylate cryptates.

The sepulchrates include derivatives of the octaazamacrobicyclic system such as 1,3,6,8,10,13,16,19-octaazabicyclo[6,6,6]eicosane. Primary amine and carboxylate derivatives of these chelates are especially preferred. Synthesis of the chelates, as the cobalt complexes, is described in J. Amer. Chem. Soc. 104:6016 (1982). The sarcophagines include derivatives of the hexaazamacrobicyclic system such as 3,6,10,13,16,19-hexaazabicyclo[6,6,6]eicosane. Synthesis of sepulchrates and sarcophagines are described by Creaser et al. in J. Amer. Chem. Soc. 104:6016 (1982) and Geue et al. in J. Amer. Chem. Soc. 106:5478 (1984), respectively. Izatt and Christensen, Eds., Synthetic Multidentate Compounds, Academic Press (1978) and Lehn et al, Acc. Chem. Res. 11:49 (1978) describe synthesis of cryptates. Cotton & Wilkinson "Advanced Inorganic Chemistry" describe a general method of crown ether template synthesis for preparing encapsulating nitrogen-containing macrocycles. Those references are incorporated herein by reference in their entirety.

Metal ions are chosen for chelation by the magnifiers for their ability to perform their diagnostic or therapeutic role. These roles include but are not limited to enhancing images in MR imaging, gamma scintigraphic or CT scanning, or X-ray, or delivering cytotoxic agents to kill undesirable cells such as in tumors.

For use with radionuclides, such as in nuclear medicine, this invention provides the advantage of tight binding of the radionuclides by the macrocyclic chelants. This allows a more specific image due to lower background levels of the metals.

By suitable selection of chelated species, chelates according to the invention may be produced which are capable of functioning as X-ray agents (for example by choosing tungsten) or as both MR and X-ray contrast agents by choosing an appropriate lanthanide metal ion.

For X-ray applications, to extend the photon energy range over which the polychelates of the invention are optimally effective the polychelates used may be of two or more different metals, either as mixtures of homopolychelates or as a heteropolychelate.

Metals that can be incorporated, through chelation, include lanthanides and other metal ions, including isotopes and radioisotopes thereof, such as, for example, Mg, Ca, Sc, Ti, B, V, Cr, Mn, Fe, Co, Ni, Cu, Zn, Ga, Sr, Y, Zr, Tc, Ru, In, Hf, W, Re, Os, Pb and Bi. Particularly preferred radioisotopes of some of the foregoing include $^{153}$Sm, $^{64}$Cu, $^{67}$Cu, $^{67}$Ga, $^{68}$Ga, $^{89}$Sr, $^{88}$Y, $^{90}$Y, $^{99m}$Tc, $^{97}$Ru, $^{103}$Ru, $^{111}$In, $^{186}$Re, $^{188}$Re, $^{203}$Pb, $^{211}$Bi, $^{212}$Bi, $^{213}$Bi, and $^{214}$Bi. The choice of metal ion for chelation by polychelants of the invention will be determined by the desired therapeutic or diagnostic application.

As indicated above the choice of metal ions to be chelated by the polychelants of the invention depends upon the diagnostic or therapeutic technique for which the resulting polychelate is to be used. For MR imaging, the metal ions should be paramagnetic, and preferably non-radioactive. For X-ray and ultrasound imaging, heavy metal ions, e.g. with atomic numbers of at least 37, preferably at least 50, should be used, again preferably non-radioactive species. For scintigraphy or radiotherapy the metal ions should of course be ions of radioactive isotopes.

Methods of complexing metal ions with chelants and polychelants are within the level of skill in the art. Each of the metals used can be incorporated into a macrocyclic chelant moiety by one of three general methods: direct incorporation, template synthesis and/or transmetallation. Direct incorporation is preferred.

The metal ions Fe(III), Cr(III), Mn(II), Hg(II), Pb(II), Bi(III) and the lanthanides can be directly incorporated into polyaminopolycarboxylates by the following general procedure. A water-soluble form of the metal, generally an inorganic salt, is dissolved in an appropriate volume of distilled, deionized water. The pH of the solution will be below 7. An aqueous solution containing an equimolar amount of the polychelant is added to the metal solution at room temperature while stirring. The pH of the mixture is raised slowly by addition of base, typically 0.1 M NaOH, until the donor groups of the polychelant are deprotonated, generally in the pH range of 7 to 9, depending on the chelant moieties.

Particular care must be taken with the lanthanide ions to maintain the pH below 8 to avoid precipitation of the metal hydroxide. Metal incorporation into DOTA derived and related macrocyclic chelant moieties will normally be a slow process, as described in the references cited below. Specific examples of the procedure are contained in the Examples hereto and in the following references.

Choppin et al, J. Inorg. Nucl. Chem., 33:127 (1971), Margerum, Rec. Chem. Prog., 24:237 (1973) and D'Olieslager et al, J. Inorg. Nucl. Chem., 35:4255 (1973) describe direct incorporation of the lanthanides into polyaminopolycarboxylates. Margerstadt, Mag. Res. Med., 3:808 (1986) and WO-A-87/06229 describe incorporation of Gd(III) into DOTA. A method of preparing Bi and Pb complexes of DOTA is described by Kumar et al, J. Chem. Soc. Chem. Commun., 3:145 (1989). The above references are incorporated herein by reference in their entirety.

Direct incorporation of Hf, Zr, W, Hg and Ta can be performed according to well known methods. See, for example, U.S. Pat. No. 4,176,173 (Winchell).

Transmetallation is useful when the metal ion needs to be reduced to a more appropriate oxidation state for the donor atoms of the chelant moiety to bind. For example, to incorporate $^{99m}$Tc or $^{186/188}$Re, the metal ion must be reduced to Tc(V) or Re(V) by the use of reducing agents such as $SnCl_2$ or cysteine by well known methods. This method requires formation of an intermediate complex. A typical example is the reduction of $^{99m}$Tc with Sn in the presence of a weakly coordinating ligand such as glucoheptonate prior to complexation with chelants such as DOTA. These methods are well known in the radiopharmaceutical art. $^{67}$Cu utilizes tetraamine chelates such as tet A or tet B (see Bhardaredj et al., JACS, 108:1351 (1986)) to stabilize Cu(II) for reaction with stronger-binding chelants.

Template synthesis can be performed by the method described by Smith et al. in Inorg. Chem., 24:3469 (1985) and 27:4154 (1988). In the case of the HAM systems, the metal ion is incorporated into the macrocyclic chelant by building the chelant around the metal ion via template synthesis. Well-known template synthesis methods are described by Smith et al. (Supra) for lanthanide template syntheses. The sepulchrate and sarcophagine macrobicyclic chelants may be similarly prepared by a template synthesis around Co. The Co is removed by reduction to Co(II) and extraction with 15 M HBr. The metal-free chelant may then be metallated via reaction with a simple metal salt by refluxing in methanol, or by transmetallation from a donor complex such as glucoheptonate, ascorbate, acetate or citrate salts. Use of triflate and/or perchlorate salts are preferred.

The broad class of crown ethers and cryptates, especially those containing N, O, and S, can be metallated in a similar fashion using one or more of the methods described above.

The metal chelates of the polychelants of the invention, especially the bifunctional polychelants but optionally also the magnifier polychelants, may be administered to patients for imaging in amounts sufficient to yield the desired contrast with the particular imaging technique. Generally dosages of from 0.001 to 5.0 mmoles of chelated imaging metal ion per kilogram of patient bodyweight are effective to achieve adequate contrast enhancements. For most MRI applications preferred dosages of imaging metal ion will be in the range from 0.005 to 1.2, eg. 0.02 to 1.0, mmoles/kg bodyweight while for X-ray applications dosages of from 0.5 to 1.5 mmoles/kg are generally effective to achieve X-ray attenuation. Preferred dosages for most X-ray applications are from 0.8 to 1.2 mmoles of the lanthanide or heavy metal/kg bodyweight.

For X-ray applications, to extend the photon energy range over which the polychelates of the invention are optimally effective the polychelates used may be of two or more different metals, either as mixtures of homopolychelates or as a heteropolychelate.

Attachment of the magnifier to a site-directed molecule results in even greater in vivo target specificity. The molecule is preferably an antibody, antibody fragment, other protein or other macromolecule which will travel in vivo to that site to deliver the chelated metals. In the present invention the capacity of this site-directed macromolecule to travel and/or bind to its target is not compromised by the addition of the chelated metals. The number of chelates per molecule is sufficient to enhance the image of that particular target. The resulting bifunctional polychelates are distinct entities, and desirably are substantially non-crosslinked.

Preferably, metal incorporation into bifunctional polychelants is accomplished prior to attachment of the magnifier(s) to a site-directed molecule. The metal is titrated from sub-stoichiometric levels up to full incorporation, thus eliminating the need for dialysis and extensive chromatographic purification. In this manner significant losses as well as dilution are avoided. Non-specific binding of the metal ions to the site-directed molecules is also prevented. However, application of the invention to radionuclides with short half-lives may require metallation of the bifunctional polychelant as a final step, followed by simple rapid purification (e.g. gel filtration) to remove excess unbound radionuclide.

In the bifunctional polychelant, preferably one or two backbone molecules are linked to the site-directed molecule. By limiting the number of magnifiers linked to the site-directed molecule, the pharmacological behavior of the bifunctional polychelant would be expected to show high target specificity and low non-specific binding.

The bifunctional polychelants are capable of containing a large number of macrocyclic chelant moieties. This allows site-specific imaging to be enhanced beyond the levels previously available.

The bifunctional polychelants of the invention involve coupling the magnifier to a site-directed molecule. The site-directed molecules may be any of the molecules that naturally concentrate in a selected target organ, tissue, cell or group of cells, or other location in a mammalian body, in vivo. These can include amino acids, oligopeptides (e.g. hexapeptides), molecular recognition units (MRU's), single chain antibodies (SCA's), proteins, Fab fragments, and antibodies. Examples of site-directed molecules include polysaccharides (e.g. CCK and hexapeptides), proteins (such as lectins, asialofetuin, polyclonal IgG, blood clotting proteins (e.g. hirudin), lipoproteins and glycoproteins), hormones, growth factors, and clotting factors (such as PF4). Exemplary site-directed proteins include polymerized fibrin fragments (e.g., $E_1$), serum amyloid precursor (SAP) proteins, low density lipoprotein (LDL) precursors, serum albumin, surface proteins of intact red blood cells, receptor binding molecules such as estrogens, liver-specific proteins/ polymers such as galactosyl-neoglycoalbumin (NGA) (see Vera et al. in Radiology 151: 191 (1984)) N-(2-hydroxypropyl)methacrylamide (HMPA) copolymers with varying numbers of bound galactosamines (see Duncan et al., Biochim. Biophys. Acta 880:62 (1986)), and allyl and 6-aminohexyl glycosides (see Wong et al., Carbo. Res. 170:27 (1987)), and fibrinogen.

The site-directed protein can also be an antibody. The choice of antibody, particularly the antigen specificity of the antibody, will depend on the desired use of the conjugate. Monoclonal antibodies are preferred over polyclonal antibodies.

Human serum albumin (HSA) is a preferred protein for the study of the vascular system. HSA is available commercially from a number of sources including Sigma Chemical Co. Preparation of antibodies that react with a desired antigen is well known. Antibody preparations are available commercially from a variety of sources. Fibrin fragment $E_1$ can be prepared as described by Olexa et al. in J. Biol. Chem. 254:4925 (1979). Preparation of LDL precursors and SAP proteins is described by de Beer et al. in J. Immunol. Methods 50:17 (1982). The above described articles are incorporated herein by reference in their entirety.

Methods for attaching backbone polymers to antibodies and other proteins are within the level of skill in the art. Such methods are described in Pierce 1989 Handbook and General Catalog and the references cited therein, Blatter et al, Biochem., 24:1517 (1985) and Jue et al, Biochem., 17:5399 (1978). The references cited above are incorporated herein by reference in their entirety.

In general, the bifunctional polychelants are synthesized by constructing the polychelant prior to conjugating the backbone polymer to the site-directed macromolecule. In most cases, the reaction conditions used for joining the chelants to the backbone would denature proteins. Therefore, to preserve its tertiary structure and biological function an antibody or other site-directed protein will not generally be conjugated to a backbone molecule before the chelant groups have been loaded onto that backbone molecule, unless of course this can be done without denaturing the protein. Metal ions can be added to form the metal complex of the polychelants prior to or following conjugation of the magnifier to the site-directed macromolecule. Preferably, the metal will be added prior to conjugation of the polychelant to most proteins, particularly antibodies, in particular to avoid adventitious binding of the metal to the protein. However, for some metal ions such as radionuclides with a short half-life, metallation will preferably be performed following conjugation, just prior to use.

In general, known methods can be used to join the macrocyclic chelants to backbone molecules. While for preferred macrocyclic chelants, such as DOTA, the conventional mixed anhydride and cyclic anhydride conjugation techniques are ineffective, it has been found that modifying the mixed anhydride procedure by reacting a polycarboxylic macrocyclic chelant in an anhydrous medium with an amine base of sufficient strength to abstract all the carboxyl protons (i.e. a high enough pKa) yields an amine salt which can react with an alkylhaloformate (eg. isobutyl chloroformate) to produce an activated anhydride capable of conjugating to amine groups of the backbone molecule without causing the undesired cross-linking associated with prior art bifunctional polychelants. For most macrocyclic chelants tetramethylguanidine or an amine base of similar strength will be the preferred base.

More complex conjugation techniques, involving for example the use of backbone derivatized macrocyclic chelants in a manner analogous to that of Meares et al. (supra), may instead be used. Similarly the chelants can be attached to the backbone molecule by a haloacetylhalide, a phosgene or a thiophosgene method depending on the available reactive group on the chelating agent.

For macrocycles with a pendant carboxylate, including but not limited to DOTA, TETA, TRITA (1,4,7,10-tetraazacyclotridecanetetraacetic acid) and NOTA, one of the carboxylates can form an entity which can react with a primary amine group of the backbone molecule. Methods of forming a reactive entity from a carboxylate group include the modified mixed anhydride reaction for example using isobutylchloroformate (IBCF), or the formation of an "activated ester" using a carbodiimide (DCC or EDAC, cf. Pierce Catalog (1988), pages 252 and 253). Both reaction sequences give rise to a backbone polymer multiply substituted with the macrocyclic chelant moieties through stable amide linkages. The modified mixed anhydride method however is the preferred method for use in joining the carboxylate-containing macrocyclic chelants to the backbone molecule.

The modified mixed anhydride reaction is performed in an anhydrous solvent preferably with a melting point below 5° C., cooled to a temperature not lower than 5° C. or greater than about 55° C. above its freezing point. The solubilization of the chelant in the appropriate solvent is conveniently effected by preparation of the amine salt of the chelant using the amine base in situ.

The choice of base is determined by the pKa of the relevant carboxylates. For most macrocycles, tetramethylguanidine (TMG) is especially preferred. In general, bases will conveniently be selected from those bases whose pKa value exceeds the highest pKa of the macrocyclic chelant by at least 0.5, preferably 0.8, especially preferably at least 1.0. Amine bases having pKa's of at least 11, especially at least 11.3, particularly at least 12, are particularly preferred and besides TMG particular mention may be made of piperidine, quinuclidine and N-ethylpiperidine and more especially DBU (1,8-diazabicyclo[5.4.0]undec-7-ene) and DBN (1,5-diazabicyclo[4.3.0]non-5-ene). Further bases are listed by Martell and Smith in "Critical Stability Constants" Vol. 5, first supplement, Plenum Press, New York 1982.

The appropriate quantity of neat (chilled) alkylhaloformate is now added with stirring and the original temperature of the solvent is maintained by cooling, e.g. by addition of coolant, if required. Isobutylchloroformate is especially preferred. The resulting activated anhydride of the macrocyclic chelant can be reacted with an amine-containing backbone molecule to form a polychelant or polychelant fragment. The polychelant, for most applications, is metallated at this point and purified by chromatography or crystallization to remove excess metal ions and lower molecular weight metal complexes. For use with target-specific molecules the magnifier polychelant, or the at least partially metallated form thereof, still containing at least one free amine, is conjugated to the targeting molecule, for example by reaction with one of many well-known heterobifunctional coupling agents. In situations where prior metallation is not appropriate, e.g. with radionuclide metal ions with short half-lives, the bifunctional polychelant can be prepared using a metal-free magnifier and coupling as described above, followed by metallation (vide infra) and final rapid, simple purification by chromatography or filtration.

The macrocyclic chelants can also be linked to a backbone molecule through a non-coordinating primary amine group. Macrocyclic chelants having a non-coordinating primary amine group include primary amine side-chain-derivatized DOTA macrocycles, primary amine-derivatized DO3A, and primary amine-derivatized hexaaza and octaaza macrocycles and macrobicycles (the HAMs, sepulchrates and sarcophagines) as well as the broad class of derivatized crown ether cryptates.

The non-coordinating primary amine group on these chelants can be reacted with a haloacetylhalide under well-known conditions to form a haloacetamide. The haloacetamide can react with a primary amine of the backbone molecule to form a stable amide linkage between the chelant and the backbone. The haloacetylhalide method described in De Riemer et al, J. Labelled Compd. Radiopharm. 18:1517 (1981) can be used to join amine-containing chelants to the backbone.

Amine groups on a macrocyclic chelant can also be reacted with phosgene to generate a reactive isocyanate group, or with thiophosgene to generate a reactive isothiocyanate group. Those groups can react with a primary amine of the backbone to form a stable urea or more stable thiourea linkage, respectively, between the ligand and the backbone polymer. Gansow, Inorg. Chimica Acta 91:213 (1984) and Moi et al, J. Amer. Chem. Soc. 110:6266 (1988) describe methods of linking chelants to proteins having an amine group through formation of the isocyanate or isothiocyanate moieties using the phosgene or thiophosgene methods, respectively. See also Desreux, Inorg. Chem. 19:1319 (1980); Bryden et al, Anal. Chem 53:1418 (1981); Delgardo et al, Talanta 29:815 (1982); Cacheris et al, Inorg. Chem. 26:958 (1987); Moi et al, Inorg. Chem 26:3458 (1987) and Meares et al, Acc. Chem. Res. 17:202 (1984).

While the backbone to which the chelants are conjugated in this fashion may be fully formed, ie it may comprise an $R^1(X^1R^2)_m$ moiety, alternatively and preferably, polychelant fragments may be conjugated onto a pre-formed polymeric backbone $R^1$. This forms a major feature of the invention. Thus in this way, each attachment site on the polymer backbone may be loaded with a plurality of chelant groups. Moreover, if the polychelant fragments are already metallated, the metal loading of the final polychelant species can be optimised as chelant groups which are not located about the periphery of the molecule may otherwise metallate inefficiently.

While for the compounds of the present invention it is preferred that $X^1$ be metabolically cleavable, conjugation of pre-formed polychelant sub-units offers a synthetic approach to other polychelants and in particular those in which $X^2$ rather than $X^1$ is cleavable, and these new compounds also form an aspect of the invention.

Accordingly, in a further aspect, the invention provides a method of preparing polychelants of formula II (wherein between each group L and $R^1$ at least one of the intervening $X^1$ and $X^2$ moieties is metabolically cleavable), said method comprising conjugating a compound of formula V $$R^1X^7_m \qquad (V)$$

with a polychelant fragment molecule of formula VI $$X^8R^2((X^2)_pL)_n \qquad (VI)$$

(where $X^7$ and $X^8$ comprise reactive groups conjugable to form a group $X^1$).

The polychelant fragments of formula VI are themselves novel and they, their chelates and their salts also form a further aspect of the present invention.

It is especially preferred to carry out this method according to the invention using metallated polychelant fragments of formula VI. In these compounds, the chelated metal is already firmly held by the macrocyclic chelant group and thus optimum metal loading of the ultimate polychelant may be achieved.

However, the chelant moieties can of course be metallated or transmetallated after the polychelant or a bifunctional polychelant derivative thereof has been formed, and such metallation or transmetallation processes form a further aspect of the present invention.

The polychelant fragment compounds of the present invention may be prepared by reaction of monochelant species with a linker molecule, followed if necessary by activation of or introduction of the reactive group $X^8$ through which the polychelant fragment molecule is in due course linked to the polymer backbone.

The polychelant fragments may be dimers, trimers or higher oligomers, but in one preferred embodiment of the present invention they are based on low generation, i.e. zero to sixth generation, dendrimeric polychelants, for example dendrimeric polychelants as described in International Patent application No. PCT/EP92/02308.

Using such dendrimeric polychelant fragment molecules poly(dendrimeric polychelants) can be produced. This may be done by reacting a dendrimer with a bifunctional linking agent so as to produce a monoderivatised dendrimer which can then be loaded with monochelant groups to produce the polychelant fragment molecule. This dendrimeric polychelant fragment molecule can be conjugated to a linear or branched polymer but will preferably be conjugated to a dendrimeric backbone.

Alternatively polychelant fragments may themselves be polymerized to produce linear or branched poly (polychelant) molecules. Such poly(polychelants) form a further aspect of the invention where they incorporate linker moieties metabolically cleavable so as to release sub-40,000 D fragments on cleavage, as do their chelates and salts and the corresponding bifunctional polychelants.

Such metabolically cleavable linker moieties can be between or within the polychelant fragments, preferably at both positions where the fragments carry more than 4 macrocyclic chelant moieties, e.g. where they are dendrimeric. Such poly(polychelants) may be represented by formula VII $$[R^2((X^2)_pL)_nX^1_q]_m \qquad (VII)$$

where $R^2$, L, p, n and m are as defined for formula II, q is a positive integer, preferably 1, 2 or 3, $X^1$ is a linker moiety linking two $R^2$ groups, $X^2$ is a linker moiety, and $X^1$ and/or $X^2$ are metabolically cleavable to yield cleavage products having molecular weights below 40,000 D, preferably below 30,000 D especially below 20,000 D.

Thus for example where the polychelant fragment is a $G_{3.0}$ polyamine starburst dendrimer of the type described by Tomalia et al (supra) loaded at 22 of its 24 amine termini with GdDO3A groups, then only about 4 such fragments need to be linked together to produce a viable blood pool imaging agent.

Viewed from another aspect therefore the invention also provides polychelant compounds of formula VIII $$(R^1)_p[R^2((X^2)_pL)_nX^1_q]_m \qquad (VIII)$$

(where each p is 0 or 1; n and m are each positive integers having values of at least 2 and being such that the total number of L moieties is at least 20; q is a positive integer, eg 1 to 100; $X^1$ and where present $X^2$ are metabolically cleavable moieties, each $X^1$ serving to link a $R^2((X^2)_pL)_n$ moiety to a $R^1$ moiety or to another $R^2((X^2)_pL)_n$ moiety; each L is a macrocyclic chelant moiety; $R^1$ where present is a linear or branched polymeric moiety; and each $R^2$ is a linear or branched backbone moiety; the compound in its unmetallated form having a molecular weight of at least 30000 D and the fragments resulting from metabolic cleavage of the $X^1$ and where present $X^2$ moieties having molecular weights below 30000 D in their unmetallated forms) and chelates, salts and conjugates thereof with site-directed molecules.

Examples of reaction schemes suitable for the preparation of polychelant and polychelant fragment molecules according to the invention include the following:

(A)
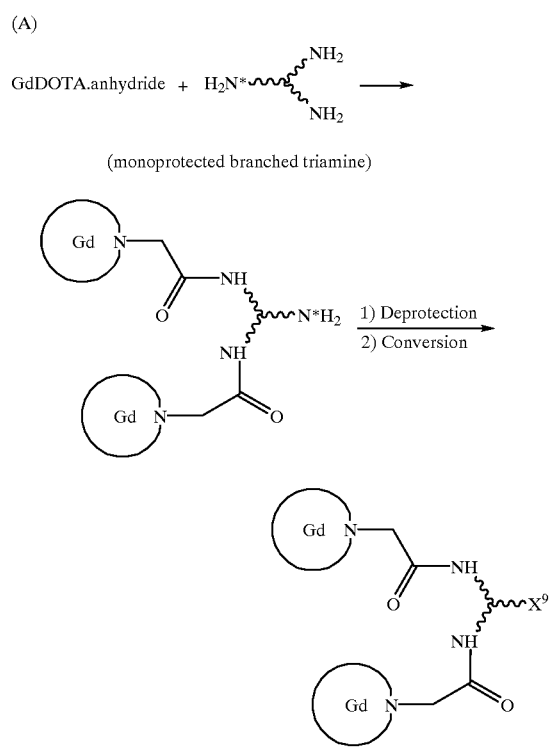
(where X⁹ = NCS, NCO, NHCOCH₂Cl
〜 = backbone, eg alkylene chain
N*H₂ = protected amine
⬭ = N-attached GdDO3A residue)
(B)
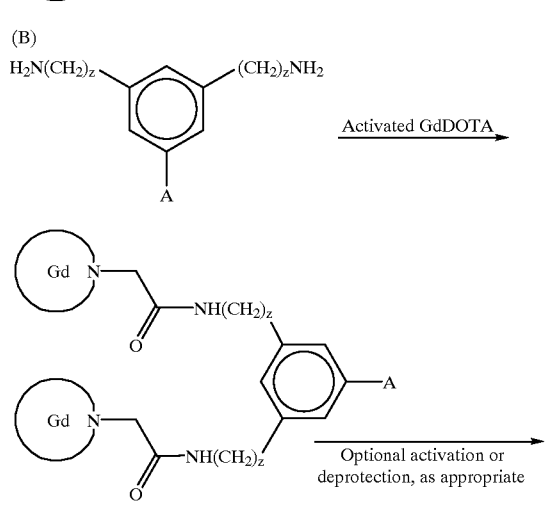
(C)
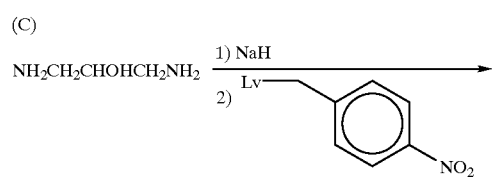
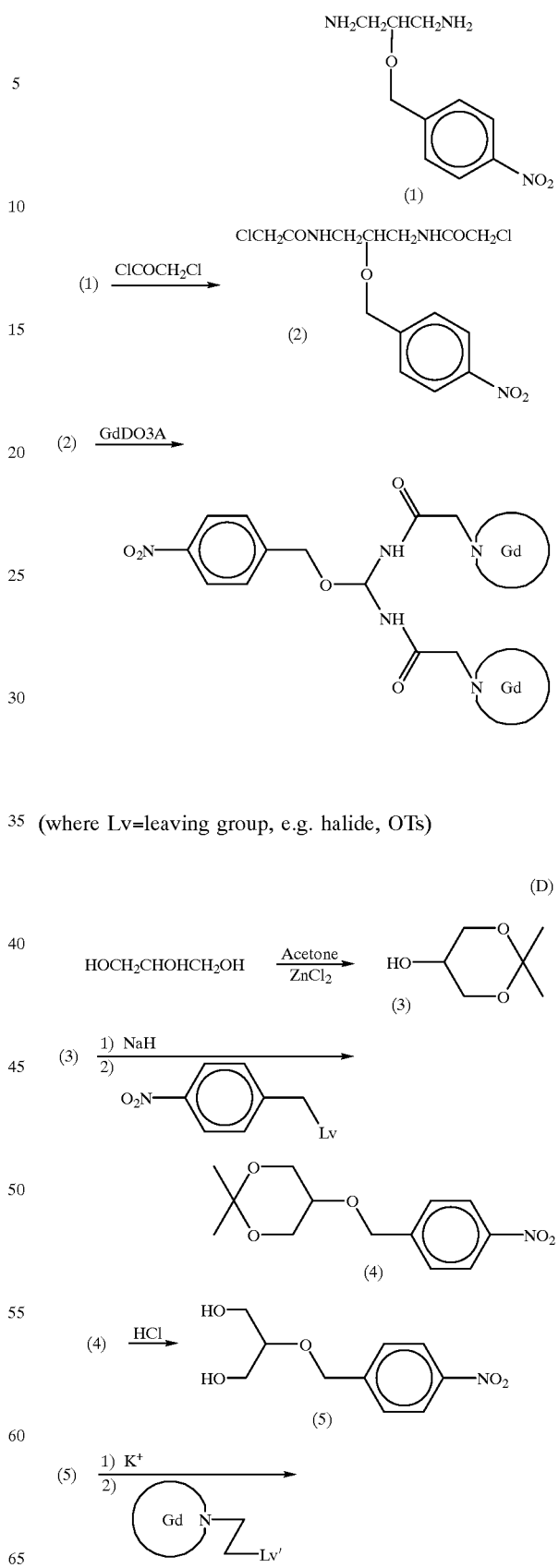
(where Lv=leaving group, e.g. halide, OTs)

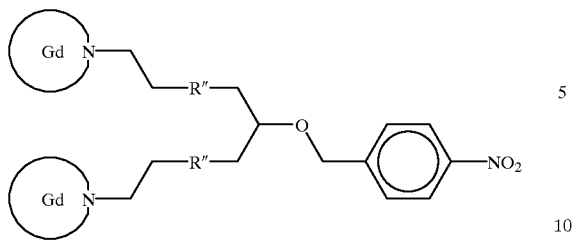
5
10
(where Lv'=OTs, OMs, Br, etc and R"=O, CONH, NHCO, etc)
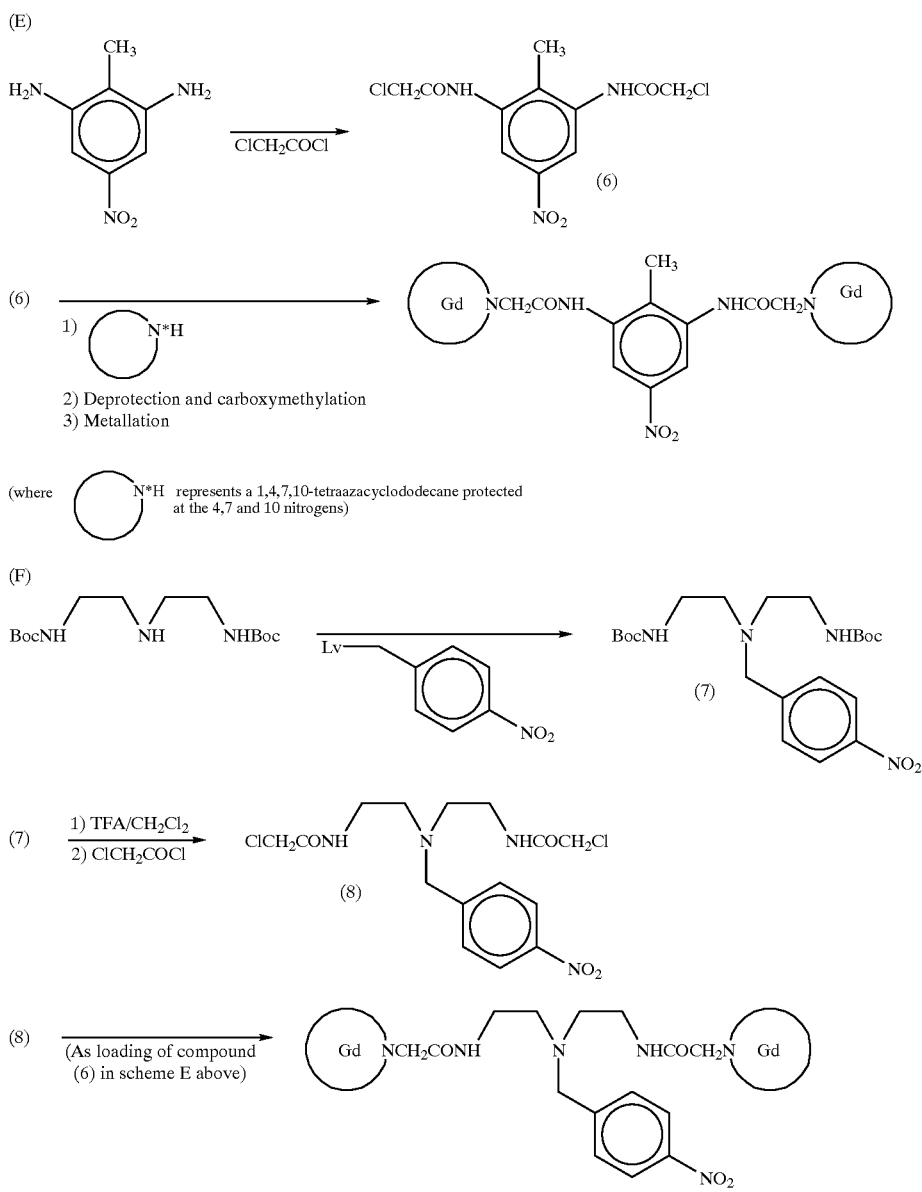

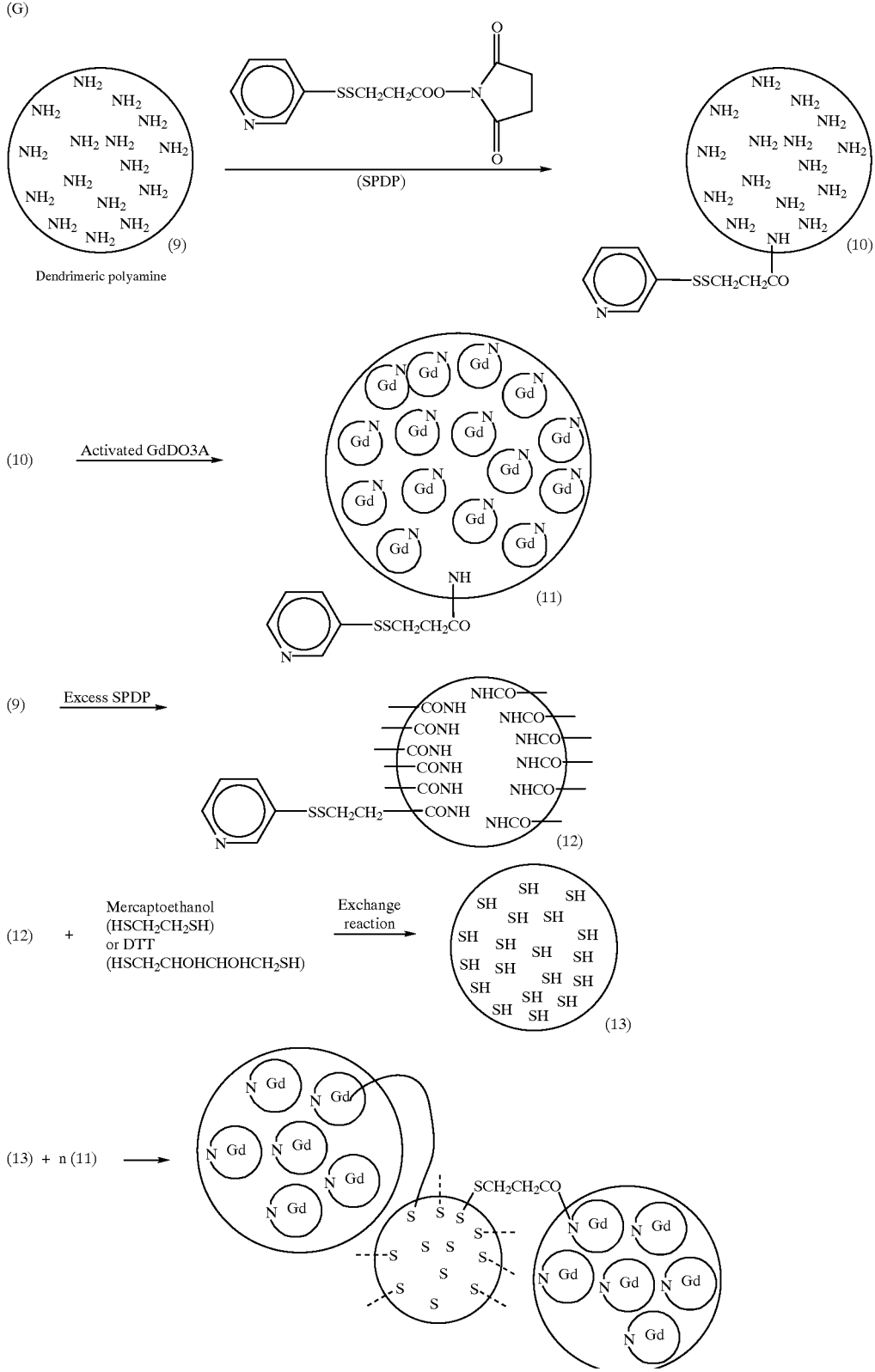

(where
SSS=solid state support, eg Merrifield resin,
$X^{10}$=SSS attachment site,
$X^{11}=X^{10}$ cleavage residue,
activated GdDO3A=eg GdDO3A with ring NH substituted by for example
CH$_2$CONHCH$_2$CH$_2$NCS or

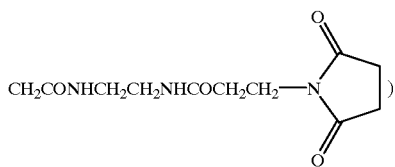

In the schemes outlined above,

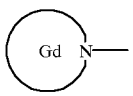

is indicated as representing a gadolinium loaded DO3A residue. However, it may also represent any other metal-loaded or unloaded macrocyclic chelant residue attached at a ring heteroatom or a ring carbon. In the event that unmetallated chelant moieties are used, metallation may be effected at an intermediate stage during preparation of the polychelant fragment molecule, after preparation of the polychelant fragment molecule or even after preparation of the overall polychelant.

In the method of scheme I, the polychelant fragments are constructed on a solid state support. This may be done using processes analogous to those described for peptide synthesis by Stewart and Young in "Solid State Peptide Synthesis", 2nd Edition, 1984, Pierce Chemical.

Where, as in schemes G, H and I, the polychelant fragments are dendrimeric polychelants, it is preferred that these have molecular weights in the unmetallated state in the range 5 to 25 kD and that the poly(polychelant) constructed therewith should contain 3 to 10, preferably 3 to 6, such fragments.

Besides the methods discussed above, other methods for linking dendrimeric polychelant fragments together may be used. In this regard, attention is drawn to the techniques discussed by Torchilin et al. in Critical Reviews in Therapeutic Drug Carrier Systems 7:275–308 (1991), U.S. Pat. No. 4737550 (Tomalia et al.) and Brinkley, Bioconjugate Chem 3:2–13 (1991).

The compounds of the present invention may be formulated with conventional pharmaceutical or veterinary aids, for example emulsifiers, fatty acid esters, gelling agents, stabilizers, antioxidants, osmolality adjusting agents, buffers, pH adjusting agents, etc., and may be in a form suitable for parenteral or enteral administration, for example injection or infusion or administration directly into a body cavity having an external escape duct, for example the gastrointestinal tract, the bladder or the uterus. Thus the compounds of the present invention may be in conventional pharmaceutical administration forms such as tablets, capsules, powders, solutions, suspensions, dispersions, syrups, suppositories etc.; however, solutions, suspensions and dispersions in physiologically acceptable carrier media, for example water for injections, will generally be preferred.

The compounds according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized. Suitable additives include, for example, physiologically biocompatible buffers (as for example, tromethamine hydrochloride), additions (e.g., 0.01 to 10 mole percent) of chelants (such as, for example, DTPA, DTPA-bisamide or non-complexed magnifier polychelant) or calcium chelate complexes (as for example calcium DTPA, CaNaDTPA-bisamide, calcium-magnifier polychelant or CaNa salts of magnifier polychelants), or, optionally, additions (e.g., 1 to 50 mole percent) of calcium or sodium salts (for example, calcium chloride, calcium ascorbate, calcium gluconate or calcium lactate combined with metal chelate complexes of magnifier ligands, and the like).

If the compounds are to be formulated in suspension form, e.g., in water or physiological saline for oral administration, a small amount of soluble chelate may be mixed with one or more of the inactive ingredients traditionally present in oral solutions and/or surfactants and/or aromatics for flavoring.

For MR and X-ray imaging of some portions of the body the most preferred mode for administering metal chelates as contrast agents is parenteral, e.g., intravenous administration. Parenterally administrable forms, e.g., intravenous solutions, should be sterile and free from physiologically unacceptable agents, and should have low osmolality to minimize irritation or other adverse effects upon administration, and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the chelates and which will not interfere with the manufacture, storage or use of products.

Viewed from a further aspect the invention provides an image enhancing or therapeutic composition comprising a metal chelate of a polychelant of the invention or a salt thereof together with at least one pharmaceutical carrier or excipient.

Viewed from a still further aspect the invention provides the use of a polychelant according to the invention or a chelate or salt thereof for the manufacture of an image enhancing contrast medium or a therapeutic composition.

Viewed from another aspect the invention provides a method of generating an image of a human or non-human animal, especially mammalian, body which method comprises administering to said body an image enhancing amount of a polychelate according to the invention or a salt thereof and thereafter generating an image e.g. an MR, X-ray, ultrasound or scintigraphic image, of at least a part of said body.

Viewed from a still further aspect the invention provides a method of radiotherapy of the human or animal body said method comprising administering to said body a therapeutically effective amount of a radioactive metal chelate of a polychelant according to the invention.

Viewed from another aspect the invention provides a detoxification composition comprising a polychelant according to the invention or a weak chelate complex or salt thereof with physiologically tolerable counterions, together with a pharmaceutical carrier or excipient.

Viewed from a still further aspect, the invention provides a method of metal detoxification comprising administering to a human or non-human animal a detoxifying amount of a polychelant according to the invention or a weak chelate complex or salt thereof with physiologically tolerable counterions.

We claim:

1. A compound of the following formula $R^1\text{—}(X^1\text{—}R^2\text{—}(X^2\text{—}L)_n)_m$ wherein $R^1$ is a dendrimeric backbone moiety;

each of $X^1$ and $X^2$, independently, is a metabolically cleavable linker moiety selected from the group consisting of ester, disulphide, acetal, ketal, anhydride, lactam, urea, double ester, and carbamate groups;

each $R^2$ is a straight chain or branched backbone moiety;

each L is a macrocyclic chelant moiety having 9 to 25 ring members;

each $R^2\text{—}(X^2\text{—}L)_n$ is a dimeric or dendrimeric polychelant fragment;

each n is an integer having a value of at least 2;

each m is an integer having a value of at least 2, said compound having at least 20 L groups and a molecular weight of at least 30 kD, and, when metabolized, releasing an $R^1$-containing fragment of a molecular weight of at most 40 kD and an $R^2$-containing fragment of a molecular weight of at most 30 kD;

or a metal chelate or a salt thereof.

2. A compound as claimed in claim 1, wherein the $R^1$-containing fragment of said compound is monodisperse.

3. A compound as claimed in claim 1, wherein $R^1$ is a first to sixth generation dendrimer.

4. A compound as claimed in claim 1, wherein the $R^2$-containing fragment of said compound is monodisperse.

5. A compound as claimed in claim 1 having a molecular weight in the range of 50 to 150 kD.

6. A compound as claimed in claim 1, wherein L is a metallated chelant moiety.

7. A compound as claimed in claim 6, wherein L is metallated with a paramagnetic metal or heavy metal ions or with radionuclides.

8. A compound as claimed in claim 7, wherein L is metallated with a paramagnetic lanthanide ions.

9. A compound as claimed in claim 1, wherein said compound is conjugated to a biodistribution modifying agent.

10. A composition comprising a compound as claimed in claim 1 together with at least one physiologically tolerable carrier or excipient.

11. A process for the preparation of a chelate of a chelate compound as claimed in claim 1, said process comprising metallating chelant groups L.

12. A process for the preparation of a compound as claimed in claim 1, said process comprising conjugating to a dendrimeric backbone compound a plurality of polychelant fragment compound of the formula $R^2\text{—}(X^2\text{—}L)_n$, where $R^2$, $X^2$, L, and $_n$ are defined in claim 1, said polychelant fragment compound optionally being in metallated form.

13. A method of generating an image of a human or non-human animal body which method comprises administering to said body an image enhancing amount of a polychelate of a compound according to claim 1 or a salt thereof and thereafter generating an image of at least a part of said body.

14. A method of radiotherapy of the human or animal body, said method comprising administering to said body a therapeutically effective amount of a radioactive metal chelate of a compound as claimed in claim 1.

* * * * *